(12) United States Patent
Meijer et al.

(10) Patent No.: US 7,501,261 B2
(45) Date of Patent: Mar. 10, 2009

(54) DETECTION OF HPV-INDUCED INVASIVE CANCERS AND THEIR PRECURSOR LESIONS WITH INVASIVE POTENTIAL

(75) Inventors: Christophorus Joannes Lambertus Maria Meijer, Leiden (NL); Renske Daniela Maria Steenbergen, Amsterdam (NL); Petrus Josephus Ferdinandus Snijders, Amstelveen (NL)

(73) Assignee: Stiching Researchfonds Pathologie, Amsterdam (NL)

( * ) Notice: Subject to any disclaimer, the term of this patent is extended or adjusted under 35 U.S.C. 154(b) by 378 days.

(21) Appl. No.: 10/551,584

(22) PCT Filed: Feb. 17, 2004

(86) PCT No.: PCT/NL2004/000118

§ 371 (c)(1),
(2), (4) Date: Nov. 3, 2005

(87) PCT Pub. No.: WO2004/087962

PCT Pub. Date: Oct. 14, 2004

(65) Prior Publication Data

US 2006/0252029 A1    Nov. 9, 2006

(30) Foreign Application Priority Data

Mar. 31, 2003    (EP) .................................. 03075928

(51) Int. Cl.
*C12P 21/06*    (2006.01)
(52) U.S. Cl. .......................................... 435/69.1; 435/6
(58) Field of Classification Search ............... 435/69.1, 435/6
See application file for complete search history.

(56) References Cited

U.S. PATENT DOCUMENTS

| 6,355,424 B1 | 3/2002 | Lorincz |
| 6,596,493 B1 | 7/2003 | Reeves |

FOREIGN PATENT DOCUMENTS

| WO | WO 99/29890 | 6/1999 |
| WO | WO 992980 | 6/1999 |
| WO | WO 02/14557 | 2/2002 |
| WO | WO 02/14557 A | 2/2002 |

OTHER PUBLICATIONS

List Heinz-Joachim et al.: "Methylation sensitivity of the enhancer from the human papillomavirus type 16" Journal of Biological Chemistry, vol. 269, n. 16, 1994, pp. 11902-11911.
Pulido Hugo Arias et al.: "Identification of a 6-cM minimal deletion at 11q23.1-23.2 and exclusion of PPP2R1B gene as a deletion target in cervical cancer" Cancer Research, vol. 60, No. 23, Dec. 1, 2000, pp. 6677-6682.
Fukuhara Hiroshi et al.: "Promoter methylation of TSLC1 and tumor supression by its gene product in human prostate cancer" Japanese Journal of Cancer Research, vol. 93, No. 6, Jun. 2002, pp. 605-609.
Steenbergen Renske D M et al.: "TSLC1 gene silencing in cervical cancer cell lines and cervical neoplasia." Journal of the National Cancer Institute, Feb. 18, 2004, vol. 96, No. 4, Feb. 18, 2004, pp. 294-305.
International Search Report.
Fukuhara, H. et al., "Promoter Methylation of TSLC1 and Tumor Suppression by Its Gene Product in Human Prostate Cancer," Jpn. J. Cancer Res., 2002, 605-609, vol. 93.
Steenbergen, R. et al., "TSLC1 Gene Silencing in Cervical Cancer Cell Lines and Cervical Neoplasia," Journal of the National Cancer Institute, 2004, 294-305, vol. 96, No. 4.
Pulido, H. et al., "Identification of a 6-cM Minimal Deletion at 11q23.1-23.2 and Exclusion of PPP2R1B Gene . . . ," Cancer Research, 2000, 6677-6682, vol. 60.
List, H-J. et al., "Methylation Sensitivity of the Enhancer from the Human . . . ," The Journal of Biological Chemistry, 1994, 11902-11911, vol. 269, No. 16.

*Primary Examiner*—Ali R. Salimi
(74) *Attorney, Agent, or Firm*—Robert D. Katz, Esq.; Cooper & Dunham LLP

(57) ABSTRACT

The invention is in the field of medicine and is concerned with a molecular diagnostic marker for progression to invasiveness of HPV-induced premalignant lesions and future metastatic potential of HPV-induced premalignant lesions and carcinomas. In particular the present invention relates to the use of the TSLC1 gene as marker for progression to invasive cervical cancer and metastatic potential of cervical lesions. The invention provides methods for detecting HPV-induced invasive cancers and their precursor lesions associated with tumor suppressor lung cancer 1 (TSLC1), comprising contacting a target cellular component of a test cell with a reagent that detects TSLC1 and detecting a reduction in the TSLC1 as compared to that of a comparable normal cell. The invention also provides molecular diagnostic markers for premalignant cervical lesions with invasive potential associated with tumor suppressor lung cancer 1 (TSLC1) in cytologically abnormal cervical smears and/or biopsies.

5 Claims, 2 Drawing Sheets

```
 -895  ccgctcttca cctgaagcct tgactaattt tttccgttgt tgtgtaatct
 -845  taaatatcta atattacaaa tatttcacac atatattcaa cacacaccta
 -795  tatattaaaa ccagggagga gaccctcgac aagcggagga gcctgagcat
 -745  accctcctcg atctaccttt cccgagattc tgccgcaaaa agaccgactg
 -695  gaaaatctca gaacccgact ctacggctgc cttctccaac tatccccgag
 -645  tctaccgcta ggctgttgag cgggctctcc cgctccgccg gacgtgcaaa
 -595  gcacgcatgc acttctccca gattgttttg tcaatccggg gacctgcctt
 -545  cttactctcc actcccgcac agccccgtt cccaaagatc tattccttcg
 -495  gtgcaaggtg agtgacggaa atttgcaacg tctggttcgc taggccagat
 -445  gcactcggtg tgcgggacag aggaccctct taagggagat tctccagtcg
 -395  tcggtctgat acagcgattg ctataaacat tcctaataaa ggtgtacaag
 -345  aagctagacc cgcccctgg agcccgagtc cttgcacgcc aggcgcccgg
 -295  gagaacactt tttccttgat ccggggaaag caaaacccga attttaacat
 -245  aaacatattt gcatacgccc ctcccttgg ccccgcccct aggtggcgcg
 -195  ggcgcgccgc cgaacgccag cgccaggggg cggggtgggg gagggagcga
 -145  ggccctccga gagccgggtt gggctcgcgg cgctgtgatt ggtctgcccg
 - 95  gactccgcct ccagcgcatg tcattagcat ctcattagct gtccgctcgg
 - 45  gctccggagg cagccaacgc cgccagtctg aggcaggtgc cgacatggc
 +  6  gagtgtagtg ctgccgagcg gatcccagtg tgcggcggca gcggcggcgg
 + 56  cggcgcctcc cgggctccgg ctccggcttc tgctgttgct cttctccgcc
 +106  gcggcactga tccccacagg tgatgggcag aatctgttta cgaaagacgt
 +156  gacagtgatc gagggagagg ttgcgaccat cagttgccaa gtcaataaga
 +206  gtgacgactc tgtgattcag ctactgaatc ccaacaggca gaccatttat
 +256  ttcagggact tcaggccttt gaaggacagc aggtttcagt tgctgaattt
 +306  ttctagcagt gaactcaaag tatcattgac aaacgtctca atttctgatg
 +356  aaggaagata cttttgccag ctctataccg atccccaca ggaaagttac
 +406  accaccatca cagtcctggt cccaccacgt aatctgatga tcgatatcca
 +456  gagagacact gcggtggaag gtgaggagat tgaagtcaac tgcactgcta
 +506  tggccagcaa gccagccacg actatcaggt ggttcaaagg gaacacagag
 +556  ctaaaaggca aatcggaggt ggaagagtgg tcagacatgt acactgtgac
 +606  cagtcagctg atgctgaagg tgcacaagga ggacgatggg gtcccagtga
 +656  tctgccaggt ggagcaccct gcggtcactg gaaacctgca gacccagcgg
 +706  tatctagaag tacagtataa gccacaagtg cacattcaga tgacttatcc
 +756  tctacaaggc ttaacccggg aaggggacgc gcttgagtta acatgtgaag
 +606  ccatcgggaa gccccagcct gtgatggtaa cttgggtgag agtcgatgat
 +856  gaaatgcctc aacacgccgt actgtctggg cccaacctgt tcatcaataa
 +906  cctaaacaaa acagataatg gtacataccg ctgtgaagct tcaaacatag
 +956  tggggaaagc tcactcggat tatatgctgt atgtatacga tcccccaca
 +1006 actatccctc ctcccacaac aaccaccacc accaccacca ccaccaccac
 +1056 caccatcctt accatcatca cagattcccg agcaggtgaa gaaggctcga
 +1106 tcagggcagt ggatcatgcc gtgatcggtg gcgtcgtggc ggtggtggtg
 +1156 ttcgccatgc tgtgcttgct catcattctg gggcgctatt tgccagaca
 +1206 taaaggtaca tacttcactc atgaagccaa aggagccgat gacgcagcag
 +1256 acgcagacac agctataatc aatgcagaag gaggacagaa caactccgaa
 +1306 gaaagaaag agtacttcat ctagatcagc ctttttgttt caatgaggtg
```

```
+1356 tccaactggc cctatttaga tgataaagag acagtgatat tggaacttgc
+1406 gagaaattcg tgtgttttt tatgaatggg tggaaaggtg tgagactggg
```

DETECTION OF HPV-INDUCED INVASIVE CANCERS AND THEIR PRECURSOR LESIONS WITH INVASIVE POTENTIAL

FIELD OF THE INVENTION

The invention is in the field of medicine and is concerned with a molecular diagnostic marker for human papillomavirus (HPV)-induced invasive cancers and their precursor lesions with invasive potential such as invasive cervical cancer, premalignant cervical lesions with invasive potential and high-risk human papillomavirus (HPV)-induced non-cervical invasive cancers. In particular the present invention relates to the use of the TSLC1 gene as marker for progression to invasiveness of HPV-induced premalignant lesions and future metastatic potential of HPV-induced premalignant lesions and carcinomas, allowing for a better risk assessment and treatment option for the individual patient.

BACKGROUND OF THE INVENTION

Cancer of the uterine cervix is the second most common cancer in women world-wide and is responsible for approximately 250,000 cancer deaths a year.

Cervical cancer development is characterized by a sequence of premalignant lesions, so called cervical intraepithelial neoplasia (CIN), which are graded I to III, referring to mild dysplasia (CIN I), moderate dysplasia (CIN II) and severe dysplasia/carcinoma in situ (CIN III). CIN I is also referred to as low grade squamous intraepithelial lesion (LSIL) and CIN II and CIN III together as high grade squamous intraepithelial lesion (HSIL).

Over the past decade it has been well established that cervical carcinogenesis is initiated by an infection with high-risk human papillomavirus (HPV). Expression of the viral oncogenes E6 and E7, which disturb the p53 and Rb tumor suppressor pathways, respectively, has been shown to be essential for both the onset of oncogenesis and the maintenance of a malignant phenotype. However, consistent with a multistep process of carcinogenesis, additional alterations in the host cell genome are required for progression of an hr-HPV infected cell to an invasive carcinoma.

In line with multiple events underlying cervical carcinogenesis is the observation that only a small proportion of women infected with high-risk HPV will develop high-grade premalignant cervical lesions (CIN III) or cervical cancer, and in most women with premalignant cervical lesions the lesions regress spontaneously.

However, at present no markers exist to predict which premalignant lesions will regress or ultimately progress to cervical cancer. Therefore, general medical practice comprises the treatment of all women with morphologically confirmed CIN II and CIN III, in order to prevent the development of cervical cancer. Consequently, many women are unnecessarily treated and unnecessarily worried.

SUMMARY OF THE INVENTION

It has now surprisingly been found that the tumor suppressor lung cancer 1 gene (TSLC1) is involved as a tumor suppressor gene in cervical carcinogenesis and that TSLC1 silencing, or a low level of expression of the TSLC1 gene, is an important determinant of cervical carcinogenesis. Compared to its role in the development of a subset of lung carcinomas, the silencing of TSLC1 plays an even more predominant role in cervical carcinogenesis. TSLC1 and the gene products thereof thus provide valuable molecular markers to diagnose invasive cervical lesions and/or to (better) predict which premalignant lesions have a high chance of progressing to cervical cancer.

Cervical cancer is almost exclusively associated with human papillomavirus (HPV) infection. Human papillomaviruses, constitute a group of more than 100 types of viruses, as identified by variations in DNA sequence. The various HPVs cause a variety of cutaneous and mucosal diseases. Certain types may cause warts, or papillomas, which are benign (noncancerous) tumors. Others have been found to cause invasive carcinoma of the uterine cervix.

HPVs are broadly classified into low-risk and high-risk types, based on their ability to induce malignant changes in infected cells. Low risk HPV types such as 1, 2, 4, 6, 11, 13 and 32 are primarily associated with benign lesions or common warts while the high risk types, such as 16, 18, 31, 33, 35, 39, 45, 51, 52, 56, 58, 59, 68, 73 and 82 are primarily associated with premalignant and malignant epithelial lesions. These high-risk types of HPV cause growths that are usually flat and nearly invisible, as compared with the warts caused by low-risk types, e.g. HPV-6 and HPV-11.

Therefore, the present invention is not only suited to detect invasive cervical cancer associated with tumor suppressor lung cancer 1 (TSLC1), but also other invasive cancers that are induced by HPV, particularly of the high-risk type and provides a method for the risk assessment of premalignant lesions becoming invasive.

Accordingly, the present invention provides methods of detecting HPV-induced invasive cancers and their precursor lesions associated with tumor suppressor lung cancer 1 (TSLC1) in a subject in need thereof, said method comprising contacting a cell component of a test cell of the subject with a reagent that detects the level of the cell component in the test cell and determining a modification in the level of the cell component in the test cell as compared with a comparable healthy cell, wherein the cell component indicates the level of TSLC1 in the cell and the modification indicates the presence of HPV-induced invasive cancer.

Very suitable HPV-induced invasive cancers or precursor lesions thereof in the context of the present invention are invasive cervical cancers and premalignant cervical lesions with invasive potential, but also invasive cancers and premalignant lesions that are induced by HPV in other tissues such as from oral cavity, oropharynx, anus, rectum, penis, vulva, etc.

A test cell may be a neoplastic cell, a proliferating cervical cell, or any other cell wherein the presence of an HPV-induced invasive cancer or precursor lesion thereof associated with tumor suppressor lung cancer 1 is to be detected.

In another embodiment, the present invention provides methods of detecting HPV-induced invasive cancers and their precursor lesions associated with tumor suppressor lung cancer 1 (TSLC1) in a subject in need thereof, said method comprising contacting a target cellular component of a test cell with a reagent that detects TSLC1 and detecting a reduction in the TSLC1 as compared to that of a comparable normal cell. Preferably in said detection an increased methylation of the TSLC1 promoter in the test cell and/or a reduced production of TSLC1 in the test cell as compared to the comparable normal cell is determined.

In yet another embodiment, the present invention provides methods of treating high-risk HPV-induced invasive cancers and their precursor lesions associated with modification of TSLC1 production in test cells in a subject in need thereof, said method comprising contacting cells of a patient suffering from said cancer with a therapeutically effective amount of a reagent that increases TSLC1 level in test cells.

In another aspect, the present invention relates to the use of molecular diagnostic markers for the detection of HPV-induced invasive cancers and their precursor lesions associated with tumor suppressor lung cancer 1 (TSLC1), wherein said marker indicates TSLC1 promoter methylation, expression of mRNA associated with production of TSLC1 polypeptide and/or allelic loss of the 11q23 chromosome. By such use, the risk of progression to invasive cancer may be determined.

BRIEF DESCRIPTION OF THE DRAWINGS

FIG. 1 shows the 5' regulatory region (−895 to −1) and coding and transcribed 3' non-coding sequences to 1456 (SEQ ID NO:1), derived from accession start and stop codons are represented in italics and are underlined.

DETAILED DESCRIPTION OF THE INVENTION

"Expression" refers to the transcription of a gene into structural RNA (rRNA, tRNA) or messenger RNA (mRNA) and, if applicable, subsequent translation into a protein.

The term "HPV-induced invasive cancer" refers to a carcinoma induced by high-risk HPV, which invades surrounding tissue.

The term "invasive cervical cancer" refers to a cervical carcinoma invading surrounding tissue.

The terms "premalignant lesion" and "precursor lesion" refer to a stage in the multistep cellular evolution to cancer with a strongly increased chance to progress to a carcinoma. With classical morphology the pathologist is unable to predict in the individual patient which of these lesions will progress or regress. The current patent application refers to a method, which can predict the progression to invasive cancer.

The term "invasive potential" refers to the potential to invade surrounding tissue and consequently to become malignant.

The term "premalignant cervical lesion" refers to a stage in the multistep cellular evolution to cervical cancer with a strongly increased chance to progress to a cervical carcinoma. With classical morphology the pathologist is unable to predict in the individual patient which of these lesions will progress or regress.

The term "capable of specifically hybridizing to" refers to a nucleic acid sequence capable of specific base-pairing with a complementary nucleic acid sequence and binding thereto to form a nucleic acid duplex.

A "complement" or "complementary sequence" is a sequence of nucleotides which forms a hydrogen-bonded duplex with another sequence of nucleotides according to Watson-Crick base-paring rules. For example, the complementary base sequence for 5'-AAGGCT-3' is 3'-TTCCGA-5'.

The term "stringent hybridization conditions" refers to hybridization conditions that affect the stability of hybrids, e.g., temperature, salt concentration, pH, formamide concentration and the like. These conditions are empirically optimised to maximize specific binding and minimize non-specific binding of the primer or the probe to its target nucleic acid sequence. The terms as used include reference to conditions under which a probe or primer will hybridise to its target sequence, to a detectably greater degree than other sequences (e.g. at least 2-fold over background). Stringent conditions are sequence dependent and will be different in different circumstances. Longer sequences hybridise specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength and pH) at which 50% of a complementary target sequence hybridises to a perfectly matched probe or primer. Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1 M NaCl, 1% SDS at 37° C. and a wash in 2×SSC at 40° C. Exemplary high stringency conditions include hybridization in 50% formamide, 1 M NaCl, 1% SDS at 37° C., and a wash in 0.1×SSC at 60° C. Hybridization procedures are well known in the art and are described in e.g. Ausubel et al, Current Protocols in Molecular Biology, John Wiley & Sons Inc., 1994.

The term "oligonucleotide" refers to a short sequence of nucleotide monomers (usually 6 to 100 nucleotides) joined by phosphorous linkages (e.g., phosphodiester, alkyl and arylphosphate, phosphorothioate), or non-phosphorous linkages (e.g., peptide, sulfamate and others). An oligonucleotide may contain modified nucleotides having modified bases (e.g., 5-methyl cytosine) and modified sugar groups (e.g., 2'-O-methyl ribosyl, 2'-O-methoxyethyl ribosyl, 2'-fluoro ribosyl, 2'-amino ribosyl, and the like). Oligonucleotides may be naturally-occurring or synthetic molecules of double- and single-stranded DNA and double- and single-stranded RNA with circular, branched or linear shapes and optionally including domains capable of forming stable secondary structures (e.g., stem-and-loop and loop-stem-loop structures).

The term "primer" as used herein refers to an oligonucleotide which is capable of annealing to the amplification target allowing a DNA polymerase to attach thereby serving as a point of initiation of DNA synthesis when placed under conditions in which synthesis of primer extension product which is complementary to a nucleic acid strand is induced, i.e., in the presence of nucleotides and an agent for polymerization such as DNA polymerase, and at a suitable temperature and pH. The (amplification) primer is preferably single stranded for maximum efficiency in amplification. Preferably, the primer is an oligodeoxy ribonucleotide. The primer must be sufficiently long to prime the synthesis of extension products in the presence of the agent for polymerization. The exact lengths of the primers will depend on many factors, including temperature and source of primer. A "pair of bi-directional primers" as used herein refers to one forward and one reverse primer as commonly used in the art of DNA amplification such as in PCR amplification.

The term "probe" refers to a single-stranded oligonucleotide sequence that will recognize and form a hydrogen-bonded duplex with a complementary sequence in a target nucleic acid sequence analyte or its cDNA derivative.

The TSLC1 (tumor suppressor in lung cancer 1) gene (Genbank Accession NM_014333) has originally been identified as a tumor suppressor gene in the lung cancer cell line A549 by functional complementation studies (Kuramochi et al., 2001; Nature Genet 27, 427-430). It was shown that re-expression of TSLC1 in the lung cancer cell line A549 suppressed tumorigenicity in nude mice. Moreover, loss or suppression of TSLC1 expression in other lung cancer cell lines was shown to be correlated to both tumorigenicity and spleen to liver metastasis in nude mice. TSLC1 mRNA suppression in these cell lines was found to correlate to hypermethylation of the TSLC1 promoter.

Subsequent analysis of non-small cell lung cancers (NSCLC) revealed allelic loss at 11q23.2, the TSLC1 locus, in about 40% of lung cancers and within this group of tumors with allelic loss promoter hypermethylation of the other allele could be detected in 85% of cases.

TSLC1 encodes a member of the immunoglobulin super family of cell adhesion molecules (IgCAMs), which consists of a wide variety of cell-surface molecules that are characterized by an immunoglobulin unit. The TSLC1 protein is an N-linked glycoprotein of 75 kDa, which is localized at the cell membrane and is involved in intracellular adhesion through homophilic trans-interaction (Masuda et al, 2002; J Biol Chem 277, 31014-31019).

The present inventors have now established that TSLC1 silencing is a frequent event in cervical cancer cell lines. TSLC1 silencing is found to result from TSLC1 promoter hypermethylation either or in not in combination with allelic loss. In vitro studies revealed a functional involvement of TSLC1 inactivation in both anchorage independent growth and tumorigenicity of cervical cancer cells, whereas immortality and proliferation were not affected. This points to a role for TSLC1 silencing in tumor invasion rather than proliferation. Loss of a putative tumor suppressor gene on chromosome 11 was already known to be involved in tumorigenicity of SiHa cervical cancer cells, and allelic loss at 11q22-23 has frequently been detected in invasive cervical carcinoma. These results indicate that inactivation of TSLC1 at 11q23.2 might play a crucial role in cervical cancer invasion.

Analysis of cervical tissue specimens revealed that TSLC1 promoter hypermethylation is limited to only a subset of high-grade CIN lesions but detectable in up to 58% of invasive cervical carcinomas. Moreover, TSLC1 promoter hypermethylation can specifically be detected in cervical smears derived from women with cervical cancer. From archival smears taken several years prior to cervical cancer diagnosis it is known, that TSLC1 promoter hypermethylation may be detected long time before the appearance of carcinomas. Promoter hypermethylation may occur e.g. already seven years prior to evolvement of invasive carcinomas. However the time span may vary in individual cases so that detectable hypermethylation of the TSLC1 promoter may be present from 20 years or even more to 1 year or less before the evolvement of invasive carcinoma. Analysis of cervical cancer cell lines revealed that silencing of TSLC1 expression is present in as much as 91% (10/11) of cell lines. TSLC1 silencing appeared not only associated with promoter methylation, but also with allelic loss at the TSLC1 locus and yet unknown events, suggesting that the percentage of cervical cancers showing TSLC1 promoter methylation is even an underestimation of the actual percentage of cases in which the TSLC1 gene is silenced.

Cervical cancer development is the ultimate result from an HPV infection and is as such etiologically different from the tumor types for which TSLC1 silencing has been described as a molecular marker (patent WO 02/14557), i.e. lung, prostate, pancreatic and hepatocellular cancer, all of which are unrelated to HPV. Moreover, our data are in favour of TSLC1 silencing providing a marker of progression to invasiveness rather than a proliferation marker as indicated in WO02/14557. Since TSLC1 promoter methylation could also be demonstrated in cervical smears, which are widely used in screening and triage settings, the potential impact of TSLC1 silencing as marker of progression to invasiveness and metastatic potential goes far beyond the level of tissue specimens.

Furthermore, whereas TSLC1 silencing provides a marker for the progression of an HPV infected lesion to invasiveness and metastatic potential of an HPV-infected lesion, the detection of specific HPV expression patterns as described in WO 99/29890 is not necessarily related to invasion and consequently represents a marker with a lower specificity of invasive cervical cancer.

Accordingly, the present invention provides methods of detecting HPV-induced invasive cancers and their precursor lesions associated with tumor suppressor lung cancer 1 (TSLC1) in a subject in need thereof, or indicative thereof, said method comprising contacting a cell component of a test cell of the subject with a reagent that detects the level of the cell component in the test cell and determining a modification in the level of the cell component in the test cell as compared with a comparable healthy cell, wherein the cell component indicates the level of TSLC1 in the cell and the modification indicates the presence of HPV-induced invasive cancers and their precursor lesions.

The present invention furthermore provides a method for detection of the presence or absence of cells in an individual that have the potential to evolve to invasive cervical carcinoma although those cells are not detectable as a lesion or precursor thereof by conventional means.

The present invention furthermore provides a method for assessment of prognosis for individuals undergoing cervical cancer screening allowing for stratification of future diagnostic follow-up and/or treatment of the individuals depending on the expression status of TSLC1 and/or hypermethylation status of the TSLC1 promoter, wherein individuals showing reduced TSLC1 expression compared to healthy individuals or hypermethylation of TSLC1 promoter are subjected to diagnostic follow-up procedures and/or testing intervals, or special treatment procedures.

The test cell of the subject may comprise a cell from a sample of skin cells (e.g. in the case of warts, veruccas and the like, presumably caused by cutaneous HPV infections), a sample of mucosal cells, such as cervical cells, and also other tissue such as oral cavity, oropharynx, penis, vulva, anus, rectum and other tissues wherein a cancer associated with HPV is to be detected. All such samples may be used as a sample in a method of the present invention. Preferably, a sample of a patient's cells comprise cervical cells as test cells. The cervical cells may e.g. be presented as a histological or cytological specimen. Cytological specimens comprise conventional cervical smears as well as thin layer preparations of cervical specimens.

A method of the present invention is particularly suited for the detection of HPV-induced invasive cancers and their precursor lesions associated with tumor suppressor lung cancer 1 (TSLC1) that are induced by high-risk HPVs. A method of detecting HPV-induced invasive cancers and their precursor lesions associated with tumor suppressor lung cancer 1 (TSLC1) may accordingly relate to the measurement of TSLC1 expression, such as in the form of measuring TSLC1 gene transcripts and/or subsequent proteins translated from said transcripts. Also a method of detecting HPV-induced invasive cancers and their precursor lesions may comprise measuring TSLC1 promoter methylation as an indication of TSLC1 expression capacity and/or TSLC1 protein production capacity.

FIG. 1 shows the cg-rich promoter region upstream of the atg start codon in the TSLC1 gene and the coding region for the TSLC1 protein. Methylation of the cg-rich promoter region will result in a sharply decreased transcription or even complete blockage of transcription. Therefore, the promoter region provides a positive marker sequence for the expression potential of this gene. Alternatively, the expression of the TSLC1 gene may be detected by measuring gene transcripts. As such, the coding region for the TSLC1 protein in this gene provides a marker sequence for detection of transcripts of the gene. In yet another alternative, the expression of the TSLC1 gene may be detected by measuring TSLC1 protein directly.

The test cell component contacted can thus be nucleic acid, such as DNA or RNA, preferably mRNA, or protein. When a cell component is protein, the reagent is typically an anti-TSLC1 antibody. When the component is nucleic acid, the reagent is typically a nucleic acid (DNA or RNA) probe or (PCR) primer. By using such probes or primers, gene expression products, such as mRNA may for example be detected. Alternatively, when the component is nucleic acid, the reagent may also be a restriction endonuclease, preferably a methylation sensitive restriction endonuclease for the detection of the presence of methyl groups on the test cell nucleic acid, said test cell nucleic acid then preferably being DNA.

The test cell component may be detected directly in situ or it may be isolated from other cell components by common methods known to those of skill in the art before contacting with the reagent (see for example, "Current Protocols in Molecular Biology", Ausubel et al. 1995. 4th edition, John Wiley and Sons; "A Laboratory Guide to RNA: Isolation, analysis, and synthesis", Krieg (ed.), 1996, Wiley-Liss; "Molecular Cloning: A laboratory manual", J. Sambrook, E. F. Fritsch. 1989. 3 Vols, 2nd edition, Cold Spring Harbor Laboratory Press)

Detection methods include such analyses as Southern and Northern blot analyses, RNase protection, immunoassays, in situ hybridization, PCR (Mullis 1987, U.S. Pat. Nos. 4,683, 195, 4,683,202, and 4,800,159), LCR (Barany 1991, Proc. Natl. Acad. Sci. USA 88:189-193; EP Application No., 320, 308), 3SR (Guatelli et al., 1990, Proc. Natl. Acad. Sci. USA 87:1874-1878), SDA (U.S. Pat. Nos. 5,270,184, and 5,455, 166), TAS (Kwoh et al., Proc. Natl. Acad. Sci. USA 86:1173-1177), Q-Beta Replicase (Lizardi et al., 1988, Bio/Technology 6:1197), Rolling Circle Amplication (RCA) or other methods for the amplification of DNA. In an alternative method RNA may be detected by such methods as NASBA (L. Malek et al., 1994, Meth. Molec. Biol. 28, Ch. 36, Isaac P G, ed., Humana Press, Inc., Totowa, N.J.) or TMA.

Nucleic acid probes, primers and antibodies can be detectably labeled, for instance, with a radioisotope, a fluorescent compound, a bioluminescent compound, a chemiluminescent compound, a metal chelator, an enzyme or a biologically relevant binding structure such as biotin or digoxygenin. Those of ordinary skill in the art will know of other suitable labels for binding to the reagents or will be able to ascertain such, using routine experimentation.

Other methods for detection include such analyses as can be performed with nucleic acid arrays (See i.a. Chee et al., 1996, Science 274(5287):610-614). For example, DNA arrays may be used for the detection of nucleic acids according to the invention. Such arrays comprise oligonucleotides with sequences capable of hybridizing under stringent conditions to the nucleic acid cell component of which the level is detected in a method of the present invention.

Since the present invention shows that a decreased level of TSLC1 transcription is often the result of hypermethylation of the TSLC1 gene, it is often desirable to directly determine whether the TSLC1 gene is hypermethylated. In particular, the cytosine rich areas termed "CpG islands", which lie in the 5' regulatory regions of genes are normally unmethylated. The term "hypermethylation" includes any methylation of cytosine at a position that is normally unmethylated in the TSLC1 gene sequence (e.g. the TSLC1 promoter). Hypermethylation can for instance be detected by restriction endonuclease treatment of the TSLC1 polynucleotide (gene) and Southern blot analysis. Therefore, in an invention method wherein the cellular component detected is DNA, restriction endonuclease analysis is preferred to detect hypermethylation of the TSLC1 gene. Any restriction endonuclease that includes CG as part of its recognition site and that is inhibited when the C is methylated, can be utilized. Methylation sensitive restriction endonucleases such as BssHII, MspI, NotI or HpaII, used alone or in combination, are examples of such endonucleases. Other methylation sensitive restriction endonucleases will be known to those of skill in the art.

Other methods for the detection of TSLC1 promoter hypermethylation involve bisulfite modification of DNA, in which the unmethylated cytosines are converted to an uracil whereas the methylated cytosines are protected from chemical modification. Subsequent PCR amplification and sequencing will reveal whether cytosines in CpG islands are maintained in case of methylation or replaced by a uracil in case of an unmethylated status. Another method involves the treatment a PCR amplified product generated from bisulfite modified DNA with restriction endonuclease that includes CG as part of its recognition site.

An alternative means to test for methylated sequences is a methylation specific PCR, which is also based on bisulfite modification of DNA, followed by specific PCR reactions that target CpG rich sequences.

For purposes of the invention, an antibody (i.e., an anti-TSLC1 antibody) or nucleic acid probe specific for TSLC1 may be used to detect the presence of TSLC1 polypeptide (using antibody) or TSLC1 polynucleotide (using nucleic acid probe) in biological fluids or tissues. Oligonucleotide primers based on any coding sequence region and regulatory sequence region in the TSLC1 sequence are useful for amplifying DNA, for example by PCR.

When using PCR primers, nucleic acid probes or restriction endonucleases, the 5' regulatory region and coding sequence of the TSLC1 sequence is analysed.

Any specimen containing a detectable amount of TSLC1 polynucleotide or TSLC1 polypeptide antigen can be used. Nucleic acid can also be analyzed by RNA in situ methods that are known to those of skill in the art such as by in situ hybridization. Preferred samples for testing according to methods of the invention include such specimens as (cervical) smears and/or (cervical) biopsies and the like. Preferably, cytological abnormal (cervical) smears and/or biopsies of high-grade (pre)malignant lesions are used as samples for testing. Although the subject can be any mammal, preferably the subject is human.

The invention methods can utilize antibodies immunoreactive with TSLC1 polypeptide, the predicted amino acid sequence of which is available as GenBank Accession No. BAA75822, or immunoreactive fragments thereof. An antibody preparation that consists essentially of pooled monoclonal antibodies with different epitopic specificities, as well as distinct monoclonal antibody preparations can be used. Monoclonal antibodies are made against antigen containing fragments of the protein by methods well known to those skilled in the art (Kohler, et al., Nature, 256: 495,1975).

The term antibody as used in this invention is meant to include intact molecules as well as fragments thereof, such as Fab and F(ab')2, which are capable of binding an epitopic determinant on TSLC1. Antibody as used herein shall also refer to other protein or non-protein molecules with antigen binding specificity such as miniantibodies, peptidomimetics, anticalins etc.

Monoclonal antibodies can be used in the invention diagnostic methods, for example, in immunoassays in which they can be utilized in liquid phase or bound to a solid phase carrier. In addition, the monoclonal antibodies in these immunoassays can be detectably labelled in various ways. Examples of types of immunoassays that can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays that are run in either the forward, reverse, or simultaneous modes, including immunohistochemical or immunocytochemical assays on physiological samples. Those of skill in the art will know, or can readily discern, other immunoassay formats without undue experimentation.

Monoclonal antibodies can be bound to many different carriers and used to detect the presence of TSLC1. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such using routine experimentation.

In performing the assays it may be desirable to include certain "blockers" in the incubation medium (usually added with the labeled soluble antibody). The "blockers" are added to assure that non-specific proteins, proteases, or antiheterophilic immunoglobulins to anti-TSLC1 immunoglobulins present in the experimental sample do not cross-link or destroy the antibodies on the solid phase support, or the radiolabelled indicator antibody, to yield false positive or false negative results. The selection of "blockers" therefore may add substantially to the specificity of the assays described in the present invention. A number of nonrelevant (i.e., nonspecific) antibodies of the same class or subclass (isotype) as those used in the assays (e.g., IgG1, IgG2a, IgM, etc.) can be used as "blockers". The concentration of the "blockers" (normally 1-100 µg/µL) may be important, in order to maintain the proper sensitivity yet to inhibit any unwanted interference by mutually occurring cross-reactive proteins in the specimen.

In using a monoclonal antibody for the in vivo detection of antigen, the detectably labeled monoclonal antibody is given in a dose that is diagnostically effective. The term "diagnostically effective" means that the amount of detectably labeled monoclonal antibody is administered in sufficient quantity to enable detection of the site having the TSLC1 antigen for which the monoclonal antibodies are specific. The concentration of detectably labelled monoclonal antibody which is administered should be sufficient such that the binding to those cells having TSLC1 is detectable compared to the background, depending upon the in vivo imaging or detection method employed, such as MRI, CAT scan, and the like. Further, it is desirable that the detectably labelled monoclonal antibody be rapidly cleared from the circulatory system in order to give the best target-to-background signal ratio.

As a rule, the dosage of detectably labelled monoclonal antibody for in vivo diagnosis will vary depending on such factors as age, sex, and extent of disease of the individual. The dosage of monoclonal antibody can vary from about 0.001 mg/m$^2$ tumor surface to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on whether multiple injections are given, tumor burden, and other factors known to those of skill in the art.

For in vivo diagnostic imaging, the type of detection instrument available is a major factor in selecting a given radioisotope. The radioisotope chosen must have a type of decay that is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140-250 keV range, which may be readily detected by conventional gamma cameras.

For in vivo diagnosis, radioisotopes can be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions that can be bound to the monoclonal antibodies of the invention are $^{111}$In, $^{97}$Ru, $^{67}$Ga, $^{68}$Ga, $^{72}$As, $^{89}$Zr, and $^{201}$Tl.

A monoclonal antibody useful in the invention methods can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements that are particularly useful in such techniques include $^{157}$Gd, $^{55}$Mn, $^{162}$Dy, $^{52}$Cr and $^{56}$Fe.

Other, e.g. ex vivo, diagnostic methods for the detection of TSLC1 production, TSLC1 gene expression or disorders therein, include methods wherein a sample for testing is provided, which sample comprises a cell preparation from cervical or other tissue. Preferably such samples are provided as smears. In order to provide for efficient testing schemes, cytologically abnormal (cervical) smears and/or biopsies of high-grade (pre)malignant lesions are used as samples for testing.

A cell or tissue sample obtained from a mammal, preferably a human, is suitably pretreated to allow contact between a target cellular component of a test cell comprised in said sample with a reagent that detects TSLC1 and detecting a reduction in the TSLC1 as compared to that of a comparable normal cell. Samples may be mounted on a suitable support to allow observation of individual cells. Examples of well-known support materials include glass, polystyrene, polypropylene, polyethylene, polycarbonate, polyurethane, optionally provided with layers to improve cell adhesion and immobilization of the sample, such as layers of poly-L-lysine or silane. Cervical smears or biopsies may for instance be prepared as for the Papanicolaou (Pap) test or any suitable modification thereof as known by the skilled person, and may be fixed by procedures that allow proper access of the reagent to the target component. In certain embodiments of the invention the cytological specimens are provided as conventional smear samples or thin layer preparations of cervical cells or any other kind of preparation known to those of skill in the art. If storage is required, routine procedures use buffered formalin for fixation followed by paraffin embedding, which provides for a well-preserved tissue infrastructure. In order to allow for immunohistochemical or immunofluorescent staining, the antigenicity of the sample material must be retrieved or unmasked. One method of retrieving the antigenicity of formaldehyde cross-linked proteins involves the treatment of the sample with proteolytic enzymes. This method results in a (partial) digest of the material and mere fragments of the original proteins can be accessed by antibodies.

Another method for retrieving the immunoreactivity of formaldehyde cross-linked antigens involves the thermal processing using heat or high energy treatment of the samples. Such a method is described in e.g. U.S. Pat. No. 5,244,787. Yet another method for retrieving antigens from formaldehyde-fixed tissues is the use of a pressure cooker (e.g. 2100-Retriever), either in combination with a microwave or in the form of an autoclave, such as described in e.g. Norton, 1994. J. Pathol. 173(4):371-9 and Taylor et al. 1996. Biotech Histochem 71(5):263-70.

Several alternatives to formaldehyde may be used, such as ethanol, methanol, methacarn or glyoxal, citrated acetone, or fixatives may be used in combination. Alternatively, the sample may be air-dried before further processing.

In order to allow for a detection with nucleic acid probes, the sample material must be retrieved or unmasked in case of formalin fixed and paraffin embedded material. One method involves the treatment with proteolytic enzymes and a post-fixation with paraformaldehyde. Proteolytic digestion may be preceded by a denaturation step in HCl. This method results in a (partial) digest of the material allowing the entry of probes to the target. No specific unmasking procedures are required in case of non-formalin fixed material, e.g. frozen material. Prior to hybridisation samples can be acetylated by treatment with triethanolamine buffer.

The nucleic acid probes or antibodies are then contacted with the sample material in a suitable buffer and permitted to specifically hybridize or bind to their nucleic acid or protein target. Upon specific binding of the nucleic acid probes or antibodies to the target components, labeled probes and/or antibodies may be detected by such methods as confocal laser scanning microscopy, bright field microscopy, flow cytometry optionally in combination with fluorescence associated cell sorting, or modifications of these techniques, which are well known to the person skilled in the art.

In one embodiment of a method of the invention an increased methylation of the TSLC1 promoter in the test cell and/or reduced production of TSLC1 in the test cell is detected as compared to the comparable normal cell.

The present invention also provides methods for treating a subject with HPV-induced invasive cancers associated with modification of TSLC1 production, or indicative thereof, comprising administering to a subject with the cancer a therapeutically effective amount of a reagent that increases TSLC1 expression. In HPV-induced invasive cancers associated with tumor suppressor lung cancer 1 (TSLC1), the TSLC1 nucleotide sequence is underexpressed as compared to expression in a normal cell, therefore, it is possible to design appropriate therapeutic or diagnostic techniques directed to this sequence. Thus, nucleic acid sequences that increase TSLC1 expression at the transcriptional or translational level can be used and, for example, nucleic acid sequences encoding TSLC1 (sense) could be administered to the subject with the HPV-induced invasive cancer, such as invasive cervical cancer.

The term "invasive cervical cancer" denotes malignant as well as premalignant cell populations, which often appear to differ from the surrounding tissue both morphologically and genotypically. These disorders are found to be associated with absence of or reduced expression of TSLC1. Essentially, any test cell abnormality that is etiologically linked to expression of TSLC1 could be considered susceptible to treatment using methods of the present invention that employ a reagent to increase TSLC1 expression.

Increased TSLC1 expression may be attained by suppression of methylation of TSLC1 polynucleotide when TSLC1 is under-expressed. When, upon diagnosis according to the present invention, the HPV-induced cancer detected is associated with TSLC1 expression, such methylation suppressive reagents as 5-azacytadine can be introduced to a cell. Alternatively, when, upon diagnosis according to the present invention, the invasive cervical cancer detected is associated with under-expression of TSLC1 polypeptide, a sense polynucleotide sequence (the DNA coding strand) encoding TSLC1 polypeptide, or 5' regulatory nucleotide sequences (i.e., promoter) of TSLC1 in operable linkage with TSLC1 polynucleotide can be introduced into the cell. Demethylases known in the art could also be used to remove methylation.

The present invention also provides gene therapy for the treatment of HPV-induced cancer associated with modification of TSLC1 production. Such therapy would achieve its therapeutic effect by introduction of the appropriate TSLC1 polynucleotide that contains a TSLC1 structural gene (sense), into cells of subjects having HPV-induced cancer. Schemes and procedures for effecting gene therapeutic treatment are known in the art, e.g. in WO 02/14557. Delivery of sense TSLC1 polynucleotide constructs can be achieved by using an expression vector or by using a colloidal dispersion system, preferably a recombinant expression vector, said recombinant expression vector preferably being a plasmid, a viral particle or a phage.

The polynucleotide sequences used in the methods of the invention may be the native, unmethylated sequence or, alternatively, may be a sequence in which a nonmethylatable analog is substituted within the sequence. Preferably, the analog is a nonmethylatable analog of cytidine, such as 5-azacytadine. Other analogs will be known to those of skill in the art. Alternatively, such nonmethylatable analogs could be administered to a subject as drug therapy, alone or simultaneously with a sense structural gene for TSLC1 or sense promoter for TSLC1 operably linked to TSLC1 structural gene. Preferably the TSLC1 polynucleotide used in the invention methods is derived from a mammalian organism, and most preferably from human.

Allelic loss of the TSLC1 locus (or LOH) can be detected by PCR amplification of polymorphic sequences flanking the TSLC1 gene. Both DNA from test cells and from healthy cells of the same individual are PCR amplified. The two PCR fragments representing both alleles are separated on a polyacrylamide gel or by capillary electrophoresis. PCR products derived from DNA of a healthy cells and of test cells are compared, wherein loss of one of two PCR fragments in test cells is indicative of an allelic loss/genetic deletion of TSLC1 locus.

The present invention also provides a kit of parts for use in a method of detecting HPV-induced invasive cancers and their precursor lesions associated with tumor suppressor lung cancer 1 (TSLC1) in test cells of a subject. Such a kit may suitably comprise a brush or spatula to take a (cervical) scrape together with a container filled with collection medium to collect test cells. Alternatively, a sampling device consisting of an irrigation syringe, a disposable female urine catheter and a container with irrigation fluid will be included to collect cervical cells by cervico-vaginal lavage.

A kit according to the present invention may comprise primers and probes for the detection of TSLC1 promoter methylation, for the detection of allele losses at chromosome 11q23.2 or for the detection of TSLC1 mRNA expression. In another embodiment, a kit according to the invention may comprise antibodies and reagents for the detection of TSLC1 protein expression in cervical scrapes or tissue specimens.

A kit of parts according to the invention comprises means for the detection of TSLC1 promoter methylation or TSLC1 expression, such as TSLC1-specific antibodies, methylation-sensitive restriction enzymes, or probes or primers capable of hybridising to the nucleotide sequence of FIG. 1.

In yet another alternative embodiment of a kit of the invention the means for the detection of TSLC1 promoter methylation or TSLC1 expression may be combined with means for the detection of HPV infection, preferably for the detection of HPV infection of the high-risk type. Such means may comprise HPV-specific primers or probes, protein markers for HPV infection or even surrogate markers for HPV infection as are known in the art.

The present invention will now be illustrated by way of the following, non limiting examples.

EXAMPLES

Example 1a

Frequent TSLC1 Silencing in Cervical Carcinoma Cell Lines

TSLC1 mRNA expression levels were measured in normal cervical epithelial cells that were derived from biopsy samples, cervical smears and 11 cervical carcinoma cell lines that contained high-risk HPV DNA. The mRNA levels were measured by real time quantitative RT-PCR using Lightcycler technology (Roche) and compared with normal primary keratinocytes. In normal cervical epithelial cells, the TSLC1 mRNA levels were comparable to those observed in primary keratinocytes. By contrast, TSLC1 mRNA was undetectable in 7 of the 11 cell lines and severely reduced in another 3 cell lines, showing that TSLC1 downregulation is apparent in 91% (10/11) of cervical carcinoma cell lines analysed.

On the other hand, TSLC1 expression was still abundant in HPV-immortalized cells. These HPV-immortalized cells are not yet tumorigenic and have previously been shown to be representative of premalignant cervical lesions in vivo.

Subsequently, the analysis of the mechanisms underlying TSLC1 downregulation was undertaken. Besides genetic events, i.e. deletions and inactivating mutations, epigenetic events may result in gene silencing, as has been described for lung cancers [Kuramochi et al., 2001].

Example 1b

Role of Methylation in TSLC1 Silencing in Cervical Cancer Cells

To assess whether a methylating event was underlying TSLC1 silencing in cervical cancer cells, the cell lines SiHa, HeLa and CaSki were treated with the methylation inhibitor 5-aza-2'-deoxycytidine. TSLC1 mRNA levels were compared to expression levels in primary epithelial cells, which was set to a 100%. Upon 5 to 7 days of incubation with 5-aza-2'-deoxycytidine TSLC1 expression levels were upregulated from 0% to 26% in SiHa, and from 4% to 70% and 0% to 33% in HeLa and CaSki cells, respectively. These data indicate that in all these 3 cell lines TSLC1 downregulation results, at least in part, from a methylating event.

Next, TSLC1 promoter methylation by radioactive bisulfite sequencing was studied. It was found that all 6 CpG sites sequenced were methylated in 9/11 cervical cancer cell lines. Except for three cell lines, no wild type sequences were detected in these cell lines, indicating that TSLC1 promoter methylation was clonal. In the remaining two cell lines none of the CpG sites were methylated. Except for one cell line, TSLC1 promoter methylation was correlated to reduced or undetectable TSLC1 mRNA expression. No TSLC1 promoter methylation was detected in 4 isolates of normal epithelial cells and in the non-tumorigenic HPV-immortalized cells.

Example 1c

Role of a Chromosomal Deletion in TSLC1 Silencing

To analyse whether a chromosomal deletion attributed to TSLC1 silencing loss of heterozygosity (LOH) analysis was performed using 8 polymorphic markers flanking the TSLC1 gene. Normal DNA derived from either lymphoblasts or fibroblasts of 8 cervical carcinoma cell lines was available. In 3 (38%) of these cell lines an allelic loss at 11q23.2 was apparent. All 3 cell lines revealed TSLC1 promoter hypermethylation and absence of detectable TSLC1 mRNA, suggesting that allelic deletion combined with promoter hypermethylation underlied complete gene silencing.

Analysis on the HPV immortalized cell lines showed an LOH at 11q23.2 in all immortal passages of one of the four cell lines. However, TSLC1 expression was still detectable in these passages and no promoter methylation was found, indicating that the retained allele is still actively transcribed. No allelic loss at 11q23 was detected in the other three cell lines.

Taken together, these data show that TSLC1 silencing in cervical cancer cells may result from 1) promoter methylation of one allele combined with deletion of the other allele as found in three of the seven cell lines that displayed reduced TSLC1 expression, 2) promoter methylation without an allelic loss, suggesting that either both alleles are hypermethylated or that one is mutated, as was found in two cell lines, or 3) other yet unknown mechanisms, as was found in two cell lines.

Example 2

TSLC1 Suppresses Anchorage Independent Growth In Vitro and Tumorigenicity in Nude Mice Malignant transformation of hr-HPV infected epithelial cells in vitro has been shown to proceed via the subsequent acquisition of 1) an immortal phenotype and 2) an anchorage independent phenotype, which can be measured by the growth of cells in soft agarose.

We tested whether TSLC1 silencing was associated with anchorage-independent cell growth by comparing the growth in soft agarose of TSLC1 expressing HPV-immortalized FK16A, FK16B, FK18A, and FK18B cells with that of the TSLC1 mRNA negative cervical cancer cell line SiHa cells. We found that the HPV-immortalized cells cultured in soft agarose produced either no colonies or a few colonies (0-100 colonies per 5000 cells). By contrast, tumorigenic cervical carcinoma SiHa cells gave rise to approximately 700-800 colonies per 5000 cells when cultured in soft agarose.

To test the hypothesis that TSLC1 gene silencing was associated with the acquisition of the anchorage-independent growth phenotype, we transfected SiHa cells with a TSLC1 expression vector or an empty control vector, selected for cells stably transfected with each plasmid, and examined their TSLC1 mRNA expression, proliferation rate, and ability to grow in soft agarose. All eight (100%) of the SiHa/TSLC1 transfectants tested expressed TSLC1 mRNA and did not show an altered proliferation rate compared with parental cells. However, seven (88%) of the eight SiHa/TSLC1 transfectants displayed a marked reduction in anchorage-independent growth compared with none of the four SiHa cells bearing the empty vector (i.e., SiHa/hygro transfectants) and untransfected SiHa cells (P=0.01) We tested four of the eight SiHa/TSLC1 transfectants for tumorigenicity by injecting them into nude mice. All (7/7; 100%) injections with untransfected SiHa cells and SiHa hygro transfectants, resulted in tumor volumes of at least 50 mm$^3$ after 2 to 6 weeks after injection compared with 0/8 (0%) injections with SiHa/TSLC1 transfectants (P<0.001). In SiHa/TSLC1 transfectants tumor volumes of at least 50 mm$^3$ were seen at 7 to 12 weeks after injection or no tumor formation was seen._The delayed tumor growth of SiHa/TSLC1 transfectants is most probably the result of the outgrowth of so called escaper cells that suppressed TSLC1.

In conclusion, these results show that TSLC1 can suppress both anchorage independent and tumorigenic growth of cervical cancer cells, leaving immortality and proliferation unaffected.

Example 3

Silencing of TSLC1 in Cervical Tissue Specimens

To determine whether and at what stage during cervical carcinogenesis TSLC1 silencing occurs in vivo, the methylation status of the TSLC1 promoter was analyzed in cervical tissue specimens.

Since the tissue specimens consist of an admixture of normal stromal components and abnormal cells the sensitivity of the assay to detect methylated CpG islands in a background of normal unmethylated DNA was determined. By analysing a dilution series of SiHa DNA (methylated TSLC1 promoter) in DNA derived from primary keratinocytes (unmethylated TSLC1 promoter), it was found that as low as 5% of methylated DNA in a background of unmethylated DNA could still be detected with high reliability, using radioactive bisulfite sequencing on a Genomyx device.

Using this method none of 15 normal cervical epithelial biopsies revealed TSLC1 promoter methylation. Similarly, TSLC1 promoter methylation was undetectable in all low grade CIN lesions (n=12). Of 20 high grade CIN lesions 35% showed methylation of the TSLC1 promoter. In addition, a total of 52 cervical squamous cell carcinoma sections were analysed, 58% (30/52) of which showed TSLC1 promoter methylation. Thus, TSLC1 promoter methylation appears to be a rather frequent event in cervical squamous cell carcinomas and occurs late during the multistep sequence of carcinogenesis. Since in addition to TSLC1 promoter hypermethylation other alterations, including an allelic loss at 11q23.2, may contribute to silencing of TSLC1 the actual percentage of TSLC1 silencing in cervical carcinomas is likely to be even higher than 58%.

Example 4

Detection of TSLC1 Promoter Methylation in Cervical Smears

In a small pilot study it was assessed whether the detection of TSLC1 alterations can be applied to cervical smears and as such be used as a marker in cervical cancer screening programs.

For this, TSLC1 promoter methylation was analysed in archival smears of women who developed cervical cancer. These scrapes were derived from a retrospective case-control which was designed to determine the value of hr-HPV testing to signal false negative cervical smears in women who developed cervical cancer and to assess whether hr-HPV is present in normal smears preceding cervical cancer (Zielinski et al., 2001; Br J Cancer 85, 398-404). TSLC1 promoter hypermethylation was analysed in archival index smears, taken from 11 women at the time of cervical cancer diagnosis, as well as the corresponding cervical cancer biopsy samples available for 10 of these women. Six (6/11; 55%) of the index smears tested positive for TSLC1 promoter hypermethylation, as did the corresponding cancer biopsy samples for those patients with an available biopsy sample.

As a follow up it was determined whether the detection of TSLC1 promoter methylation cannot only provide a diagnostic marker to detect invasive cervical cancer but may also provide a marker for risk assessment of progression to invasiveness. Five of the six patients that tested positive for TSLC1 promoter hypermethylation, had archival cervical smears that were taken up to 19 years before cervical cancer was diagnosed and which were classified as either low grade squamous intraepithelial lesion (LSIL) or high grade intraepithelial lesion (HSIL). We found that smears that were taken up to 7 years prior to cervical cancer diagnosis had detectable levels of TSLC1 promoter hypermethylation, whereas smears taken more than 7 years prior to cervical cancer diagnosis tested had not. Moreover, we found that TSLC1 promoter hypermethylation was mainly present in HSIL and rarely in LSIL, confirming that in cervical carcinogenesis the HSIL lesions are at the highest risk of having invasive potential, but that also amongst LSILs the lesions with invasive potential can be recognised.

No TSLC1 promoter methylation was detected in normal smears (n=15).

Example 5

TSLC1 Promoter Methylation Analysis by Methylation Specific PCR (MSP)

To improve the sensitivity of detecting cells with TSLC1 promoter hypermethylation in a background of normal cells without TSLC1 promoter methylation we developed two novel methylation specific PCR tests. These tests are, similar to the bisulfite sequencing analysis as described in examples 1b, 3 and 4, also based on bisulfite modification of DNA, in which the unmethylated cytosines are converted to an uracil whereas the methylated cytosines are protected from chemical modification. Each test consists of one primer pair which specifically recognizes sequences with methylated cytosines (i.e. unmodified cytosines following bisulfite treatment) and a second primer pair which specifically recognizes sequences with unmethylated cytosines (i.e. cytosine converted to uracil following bisulfite treatment).

The first set of methylated and unmethylated DNA specific primer pairs spans nt −645 to −494 with respect to ATG (FIG. 1) for the methylated primer set and nt −646 to −496 (FIG. 1) for the unmethylated primer set. The second set of methylated and unmethylated DNA specific primer pairs spans nt −414 to 258 with respect to ATG (FIG. 1) for the methylated primer set and nt −414 to −254 (FIG. 1) for the unmethylated primer set.

To improve the specificity of the test the PCR products were hybridised to internal methylated DNA and unmethylated DNA specific probes using reverse line blot hybridisation. For this purpose the reverse primers were labelled with biotine and hybridisation was essentially performed as described by van den Brule et al., J. Clin. Microbiol 2002. 40, 779-787.

A third primer set was based on a MSP described by Jansen et al. (Cancer Biol Ther. 2002 :293-6), spanning nt −695 to −582 with respect to ATG (FIG. 1) for the methylated primer set and nt −695 to −579 (FIG. 1) for the unmethylated primer set. Also in this case the reverse primer was biotinylated and internal probes were selected for reverse line blot hybridisation.

All MSPs were found to detect down to as low as 5 abnormal cells (i.e. 5 cells with TSLC1 promoter hypermethylation) in a background of 1000 normal cells (i.e. cells without TSLC1 promoter hypermethylation).

Using the combination of these MSPs in a pilot study TSLC1 promoter hypermethylation could be detected in 86% (12/14) of the cervical carcinomas analysed.

Example 6

Reduced TSLC1 Expression in Cervical Carcinomas

For the analysis whether the detection of TSLC1 promoter hypermethylation in cervical carcinomas is related to a reduced TSLC1 protein expression the following experiment was performed.

Using anti-TSLC1 antibodies TSLC1 expression can be examined in the course of an immunohistochemical staining procedure as is known to those of skill in the art. In specimens immuno-stained with the TSLC1-specific antibody TSLC1 was detected in normal cervical epithelium, but not detectable in cervical carcinoma cells. This fact is caused by TSLC1 promoter hypermethylation effecting reduced TSLC1 protein levels within the invasive carcinoma cells.

In summary, TSLC1 gene silencing is a highly frequent event in HPV-associated cervical carcinomas. It appears far more frequent than in carcinomas which are not associated with an HPV-infection and which have a different etiology. For example TSLC1 silencing has been detected in 40% of lung cancers (Kuramochi et al., 2001; Nature Genet 27, 427-430) 33% of breast cancers [Allinen et al.,], 32% of prostate cancers [Fukuhara et al., 2002], 27% of primary pancreatic adenocarcinomas [Jansen et al., 2002] and 34% of nasopharyngeal carcinoma (Bik-Yu Hui et al., 2003; Mol Carcinogenesis, 38, 170-178).

Moreover, in vitro studies revealed a functional involvement of TSLC1 silencing in progression to tumorigenicity of an HPV-transformed cell. It is likely that the absence of TSLC1 protein expression and/or the presence of TSLC1 promoter hypermethylation is not only a biomarker for the progression to invasiveness of a premalignant HPV-infected lesion but also for prognosis of invasive cervical cancers. In adenocarcinomas of the lung a reduced TSLC1 expression has indeed been associated with a poor prognosis (Uchino et al., Cancer, 2003, 98, 1002-1007).

Example 7

Reduced Expression of TSLC1 and/or TSLC1 Promoter Hypermethylation in HPV-Induced Carcinomas of the Oropharynx and their Precursor Lesions It can be expected that in the group of oropharyngeal carcinomas caused by HPV the TSLC1 promoter is hypermethylated and TSLC1 protein expression is absent or reduced in an identical way as described above for cervical carcinomas. Hence, for the analysis of HPV-associated oropharyngeal carcinomas and their precursor lesions an experiment as for example the following may be performed. Using anti-TSLC1 antibodies TSLC1 expression can be examined in the course of an immunohistochemical staining procedure as is known to those of skill in the art. Similarly, TSLC1 promoter hypermethylation can be examined on the same specimen by bisulfite sequencing as described in Example 3 or MSP procedures as described in Example 5. In oropharyngeal cancer specimens and specimens of their precursor lesions with invasive potential and consequently metastatic potential immuno-staining with anti-TSLC1 antibodies may yield a markedly reduced signal, compared to normal oropharyngeal epithelium. Moreover, the specimens with reduced immuno-staining may reveal TSLC1 promoter hypermethylation. Prediction of the invasive and metastatic potential may have major influence on individual treatment strategies of patients with HPV-associated precursor lesions of oropharyngeal cancer or invasive oropharyngeal cancer.

The invention claimed is:

1. A method of detecting an HPV-induced invasive cancer or a precursor lesion thereof associated with tumor suppressor lung cancer 1 (TSLC1) in a subject, the method comprising contacting a target cellular nucleic acid component of in a test cell with a reagent that detects TSLC1, and detecting a reduction in the TSLC1 in the test cell as compared to that of a comparable normal cell, detecting an increase or decrease in methylation of the TSCL1 promoter in the test cell, as compared to a comparable normal cell, or both.

2. A method according to claim 1, wherein the target cellular component is a nucleic acid.

3. A method according to claim 2, wherein the nucleic acid is mRNA.

4. A method according to claim 1, wherein the reagent is a nucleic acid probe or primer that binds to TSLC1.

5. A method according to claim 1, wherein the subject has loss of heterozygosity at chromosome 11q23.

* * * * *

SEQUENCE LISTING

<160> NUMBER OF SEQ ID NOS: 1

<210> SEQ ID NO 1
<211> LENGTH: 2350
<212> TYPE: DNA
<213> ORGANISM: Homo sapiens

<400> SEQUENCE: 1

```
ccgctcttca cctgaagcct tgactaattt tttccgttgt tgtgtaatct taaatatcta      60
atattacaaa tatttcacac atatattcaa cacacaccta tatattaaaa ccagggagga     120
gaccctcgac aagcggagga gcctgagcat accctcctcg atctacctt cccgagattc      180 tgccgcaaaa agaccgactg gaaaatctca gaacccgact ctacggctgc cttctccaac     240
tatccccgag tctaccgcta ggctgttgag cgggctctcc cgctccgccg gacgtgcaaa     300
gcacgcatgc acttctccca gattgttttg tcaatccggg gacctgcctt cttactctcc     360
actcccgcac agcccccgtt cccaaagatc tattccttcg gtgcaaggtg agtgacggaa     420
atttgcaacg tctggttcgc taggccagat gcactcggtg tgcgggacag aggaccctct     480
```

```
taagggagat tctccagtcg tcggtctgat acagcgattg ctataaacat tcctaataaa    540
ggtgtacaag aagctagacc cgcccctgg agcccgagtc cttgcacgcc aggcgcccgg     600
gagaacactt tttccttgat ccggggaaag caaaacccga attttaacat aaacatattt    660
gcatacgccc ctccccttgg ccccgcccct aggtggcgcg ggcgcgccgc cgaacgccag    720
cgccaggggg cggggtgggg gagggagcga ggccctccga gagccgggtt gggctcgcgg    780
cgctgtgatt ggtctgcccg gactccgcct ccagcgcatg tcattagcat ctcattagct    840
gtccgctcgg gctccggagg cagccaacgc cgccagtctg aggcaggtgc ccgacatggc    900
gagtgtagtg ctgccgagcg gatcccagtg tgcggcggca gcggcggcgg cggcgcctcc    960
cgggctccgg ctccggcttc tgctgttgct cttctccgcc gcggcactga tccccacagg   1020
tgatgggcag aatctgttta cgaaagacgt gacagtgatc gagggagagg ttgcgaccat   1080
cagttgccaa gtcaataaga gtgacgactc tgtgattcag ctactgaatc ccaacaggca   1140
gaccatttat ttcagggact tcaggccttt gaaggacagc aggtttcagt tgctgaattt   1200
ttctagcagt gaactcaaag tatcattgac aaacgtctca atttctgatg aaggaagata   1260
cttttgccag ctctataccg atcccccaca ggaaagttac accaccatca cagtcctggt   1320
cccaccacgt aatctgatga tcgatatcca gagagacact gcggtggaag gtgaggagat   1380
tgaagtcaac tgcactgcta tggccagcaa gccagccacg actatcaggt ggttcaaagg   1440
gaacacagag ctaaaaggca aatcggaggt ggaagagtgg tcagacatgt acactgtgac   1500
cagtcagctg atgctgaagg tgcacaagga ggacgatggg gtcccagtga tctgccaggt   1560
ggagcaccct gcggtcactg gaaacctgca gacccagcgg tatctagaag tacagtataa   1620
gccacaagtg cacattcaga tgacttatcc tctacaaggc ttaacccggg aaggggacgc   1680
gcttgagtta acatgtgaag ccatcgggaa gccccagcct gtgatggtaa cttgggtgag   1740
agtcgatgat gaaatgcctc aacacgccgt actgtctggg cccaacctgt tcatcaataa   1800
cctaaacaaa acagataatg gtacataccg ctgtgaagct tcaaacatag tggggaaagc   1860
tcactcggat tatatgctgt atgtatacga tccccccaca actatccctc ctcccacaac   1920
aaccaccacc accaccacca ccaccaccac caccatcctt accatcatca cagattcccg   1980
agcaggtgaa gaaggctcga tcagggcagt ggatcatgcc gtgatcggtg gcgtcgtggc   2040
ggtggtggtg ttcgccatgc tgtgcttgct catcattctg gggcgctatt ttgccagaca   2100
taaaggtaca tacttcactc atgaagccaa aggagccgat gacgcagcag acgcagacac   2160
agctataatc aatgcagaag gaggacagaa caactccgaa gaaaagaaag agtacttcat   2220
ctagatcagc cttttttgttt caatgaggtg tccaactggc cctattttaga tgataaagag   2280
acagtgatat tggaacttgc gagaaattcg tgtgtttttt tatgaatggg tggaaaggtg   2340
tgagactggg                                                          2350
```